United States Patent
Cramer et al.

[19]

[11] Patent Number: 5,925,072
[45] Date of Patent: Jul. 20, 1999

[54] DISPOSABLE ELASTIC THERMAL BACK WRAP

[75] Inventors: Ronald Dean Cramer, Cincinnati; Leane Kristine Davis, Milford; William Robert Ouellette, Cincinnati, all of Ohio

[73] Assignee: The Procter & Gamble Company, Cincinnati, Ohio

[21] Appl. No.: 08/777,830

[22] Filed: Dec. 31, 1996

[51] Int. Cl.$^6$ .................................................. A61F 7/00
[52] U.S. Cl. .......................... 607/108; 607/112; 607/114; 62/4; 165/46
[58] Field of Search ................... 607/96, 104, 108–112, 607/114; 602/2; 165/46; 126/204; 62/4

[56] References Cited

U.S. PATENT DOCUMENTS

| | | | |
|---|---|---|---|
| Re. 32,026 | 11/1985 | Yamashita et al. | 126/263 |
| 1,491,539 | 4/1924 | Kirschmann . | |
| 2,547,886 | 4/1951 | Poux | 62/1 |
| 2,562,121 | 7/1951 | Poux | 150/2.2 |
| 2,602,302 | 7/1952 | Poux | 62/1 |
| 3,463,161 | 8/1969 | Andrassy | 128/402 |
| 3,900,035 | 8/1975 | Welch et al. | 128/402 |
| 3,943,912 | 3/1976 | Nakayama | 128/1.3 |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,462,224 | 7/1984 | Dunshee et al. | 607/114 X |
| 4,470,417 | 9/1984 | Gruber | 128/402 |
| 4,516,564 | 5/1985 | Koiso et al. | 126/263 |
| 4,575,097 | 3/1986 | Brannigan et al. | 128/402 |
| 4,586,506 | 5/1986 | Nangle | 128/403 |
| 4,649,895 | 3/1987 | Yasuki et al. | 126/263 |
| 4,688,572 | 8/1987 | Hubbard et al. | 128/402 |
| 4,753,241 | 6/1988 | Brannigan et al. | 128/380 |
| 4,756,299 | 7/1988 | Podella | 126/263 |
| 4,860,748 | 8/1989 | Chiurco et al. | 128/399 |
| 4,886,063 | 12/1989 | Crews | 128/403 |
| 4,891,501 | 1/1990 | Lipton | 607/108 X |
| 4,925,743 | 5/1990 | Ikeda et al. | 428/702 |

(List continued on next page.)

FOREIGN PATENT DOCUMENTS

| | | | |
|---|---|---|---|
| 0 014 300 A1 | 8/1980 | European Pat. Off. | A61F 7/00 |
| 0 370 600 A1 | 7/1989 | European Pat. Off. | F24J 1/00 |
| 2 687 912-A1 | 9/1993 | France | A61F 5/02 |
| 160443 | 9/1983 | India | C09K 3/02 |
| 56-145846 | 11/1981 | Japan | A61F 7/03 |
| 57-170252 | 10/1982 | Japan | A61F 7/03 |
| 58-37075 | 3/1983 | Japan | C09K 5/00 |
| 3-100090 | 4/1991 | Japan | C09K 5/00 |
| 5-317188 | 12/1993 | Japan | A47J 36/28 |
| 6-1969 | 1/1994 | Japan | C09K 5/00 |
| 6-315498 | 11/1994 | Japan | A61F 7/08 |
| 6-343658 | 12/1994 | Japan | A61F 7/08 |
| 7-67907 | 3/1995 | Japan | A61F 7/08 |
| 7-124192 | 5/1995 | Japan | A61F 7/08 |
| 7-49042 | 5/1995 | Japan | A61F 7/08 |
| 7-194641 | 8/1995 | Japan | A61F 7/08 |
| 7-194642 | 8/1995 | Japan | A61F 7/08 |
| 8-98856 | 4/1996 | Japan | A61F 7/08 |
| 8-126656 | 5/1996 | Japan | A61F 7/08 |
| 2 205 496 | 12/1988 | United Kingdom | A61F 7/03 |
| WO 94/00087 | 1/1994 | WIPO | A61F 7/00 |
| WO 94/12125 | 6/1994 | WIPO | A61F 5/02 |

*Primary Examiner*—Jeffrey R. Jastrzab
*Assistant Examiner*—Ryan Carter
*Attorney, Agent, or Firm*—Loy M. White; Douglas C. Mohl; T. David Reed

[57] ABSTRACT

The present invention relates to disposable thermal back wraps having one or more thermal packs comprising a plurality of heat cells, wherein heat is applied to specific areas of the user's lower back, for pain relief. More particularly, the present invention relates to disposable elastic thermal back wraps having good conformity to user's back which provides consistent, convenient and comfortable heat application.

23 Claims, 2 Drawing Sheets

U.S. PATENT DOCUMENTS

| | | | |
|---|---|---|---|
| 4,981,135 | 1/1991 | Hardy | 607/108 |
| 5,000,176 | 3/1991 | Daniel | 128/402 |
| 5,025,777 | 6/1991 | Hardwick | 126/263 |
| 5,046,479 | 9/1991 | Usui | 126/204 |
| 5,062,414 | 11/1991 | Grim | 128/68.1 |
| 5,072,598 | 12/1991 | Dibrell | 62/259.3 |
| 5,125,392 | 6/1992 | Hardwick | 126/263 |
| 5,148,804 | 9/1992 | Hill et al. | 128/402 |
| 5,179,942 | 1/1993 | Drulias et al. | 128/101.1 |
| 5,179,944 | 1/1993 | McSymytz | 128/403 |
| 5,190,033 | 3/1993 | Johnson | 128/403 |
| 5,211,949 | 5/1993 | Salyer | 607/108 X |
| 5,233,981 | 8/1993 | Miyashita | 607/114 |
| 5,342,412 | 8/1994 | Ueki | 607/114 |
| 5,366,492 | 11/1994 | Ueki | 607/114 |
| 5,378,225 | 1/1995 | Chatman, Jr. et al. | 602/19 |
| 5,395,399 | 3/1995 | Rosenwald | 107/108 |
| 5,398,667 | 3/1995 | Witt | 126/263 |
| 5,399,150 | 3/1995 | Saunders | 602/19 |
| 5,405,671 | 4/1995 | Kamin et al. | 428/69 |
| 5,450,858 | 9/1995 | Zablotsky et al. | 128/876 |
| 5,496,357 | 3/1996 | Jensen et al. | 607/108 |
| 5,496,358 | 3/1996 | Rosenwald | 607/108 |
| 5,534,021 | 7/1996 | Dvoretzky et al. | 607/112 |
| 5,605,144 | 2/1997 | Simmons et al. | 126/204 |
| 5,674,270 | 10/1997 | Viltro et al. | 607/112 |

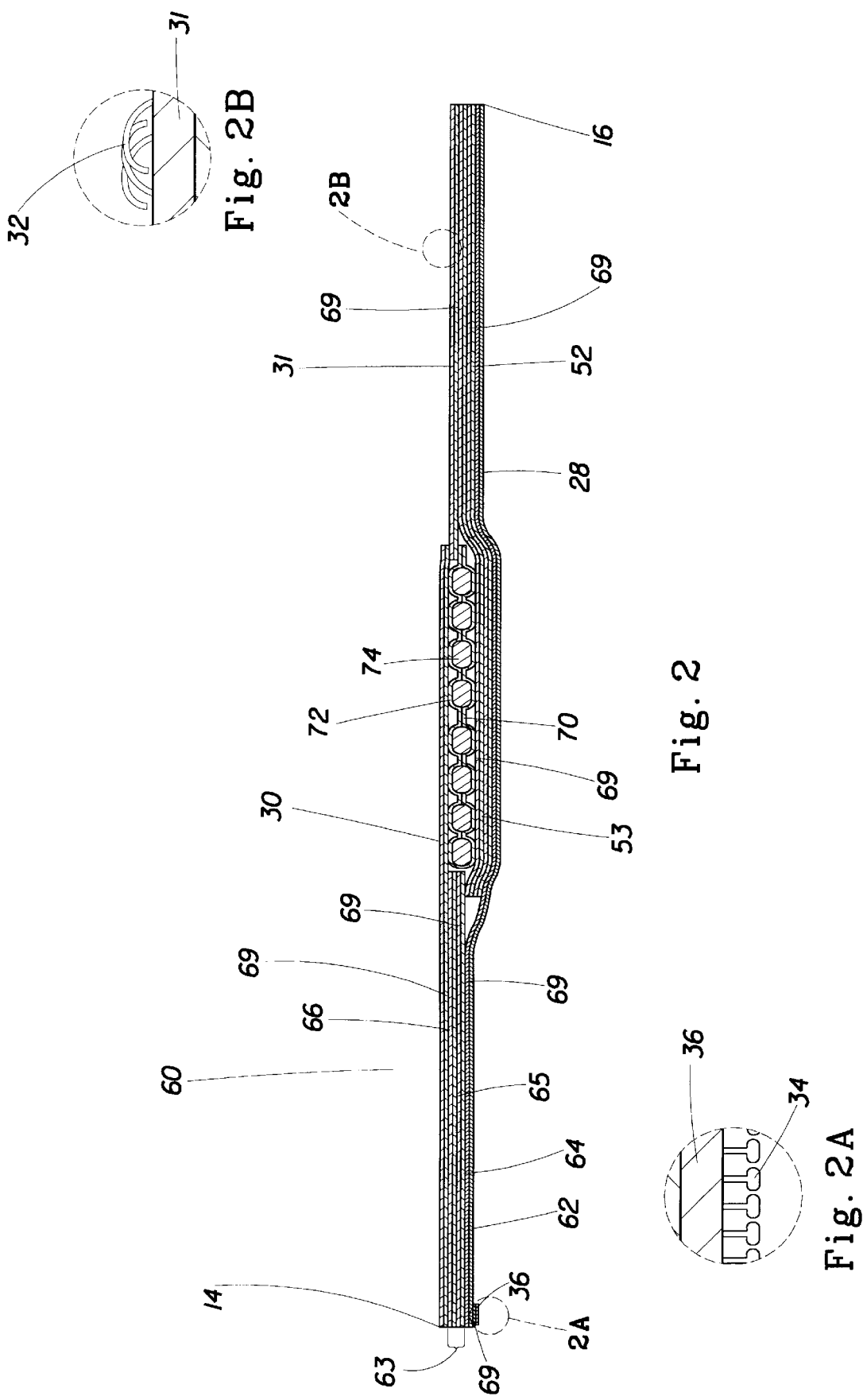

DISPOSABLE ELASTIC THERMAL BACK WRAP

TECHNICAL FIELD

The present invention relates to disposable thermal back wraps having one or more thermal packs comprising a plurality of heat cells, wherein heat is applied to specific areas of the user's lower back, for pain relief. More particularly, the present invention relates to disposable elastic thermal back wraps having good conformity to user's back which provides consistent, convenient and comfortable heat application.

BACKGROUND OF THE INVENTION

A common method of treating temporary or chronic pain is by application of heat to the afflicted area. Such heat treatments are used as a means of therapy for conditions which include aches, stiffness in muscles and joints, nerve pain, rheumatism and the like.

Chronic back pain is one of the most common complaints found in modem society. Heating pads and elastic compression bands are common devices used to relieve chronic back pain. More recently, combinations of elastic back wraps and heating pads have been available. Many of these combination devices, however, utilize thermal packs which are reusable via the replenishment of thermal energy including heated water and/or microwaveable gels. Such therapeutic devices are inconvenient to use on a regular basis.

In general, the beneficial therapeutic effects from the administration of heat diminishes after the heat source is removed. Therefore, depending on the temperature, it is desirable to provide a sustained heat source to the afflicted area for as long as possible, i.e., for from about twenty minutes to about twelve hours, preferably from about four hours to about twelve hours, most preferably from about eight hours to about twelve hours. Depending on the length of exposure, the skin temperature needs to be maintained from about 35° C. to about 55° C., preferably from about 36° C. to about 45° C., more preferably from about 37° C. to about 43° C., and most preferably from about 38° C. to about 42° C., to achieve the desired therapeutic benefits. Many of the current heating devices which require the thermal source to be replenished, such as the devices mentioned above, are inconvenient to use on a regular and extended basis because the heat energy may not be immediately available when needed or released in a controllable manner. That is, many of these thermal units or devices do not provide long lasting heat and also do not maintain a consistent temperature over long periods of time. Proper positioning of the thermal energy also may not be maintainable during use.

Disposable heat packs based on iron oxidation, such as those described in U.S. Pat. Nos. 4,366,804, 4,649,895, 5,046,479 and Re. 32,026, are known.

However, such devices have proven not totally satisfactory because many of these devices are bulky, cannot maintain a consistent and controlled temperature, have difficulty staying in place during use, and/or have unsatisfactory physical dimensions which hinder their effectiveness. Specifically, such devices cannot be easily incorporated into wraps which can comfortably conform to various body contours and hence deliver inconsistent, inconvenient and/or uncomfortable heat application to the body.

The present inventors have discovered disposable elastic thermal back wraps which provide both compression and thermal energy in a controlled and sustainable manner. These wraps comprise one or more thermal packs having a unified structure, wherein each thermal pack has at least one continuous layer of a semirigid material which is sufficiently rigid in specific areas of the thermal pack, yet which softens in between such areas when heated during use, preferably comprising a coextruded film of polypropylene and EVA. The thermal pack or packs also comprise a plurality of individual heat cells, which typically comprise an exothermic composition, preferably comprising a specific iron oxidation chemistry and having specific physical dimensions and fill characteristics, spaced apart and fixedly attached across the thermal pack. Active heat cells, that is, heat cells having a temperature of from about 39° C. to about 60° C., preferably from about 40° C. to about 48° C., more preferably from about 42° C. to about 47° C., most preferably from about 44° C. to about 45° C., preferably soften narrow portions of the continuous layer or layers of semirigid material which immediately surround the heat cells. All remaining portions of the continuous layer or layers which surround the softened portions remain more rigid. The narrow, softened portions act as hinges between each heat cell and the remaining, cooler, more rigid portions, bending preferentially more than either the heat cell or the more rigid portions. This results in thermal packs which possess sufficient rigidity to maintain structural support of the heat cells when oriented on an incline or vertically, to prevent unacceptable stretching of structures of the continuous layer or layers during processing or use, and to ensure child resistance, while still maintaining good overall drape characteristics when heated. The thermal pack or packs, when incorporated into the back wraps of the present invention, provide uniform heat coverage by having excellent conformity with the user's back.

It is therefore an object of the present invention to provide disposable elastic back wraps which comprise one or more thermal packs, each having a unified structure of at least one continuous layer of semirigid material, which has different stiffness characteristics over a range of temperatures, and a plurality of individual heat cells, which provide a controlled and sustained temperature and which reach their operating temperature range relatively quickly. The heat cells are spaced apart and fixedly attached across the unified structure of the thermal pack.

It is a further object of the present invention to provide disposable thermal back wraps having good overall drapability while maintaining sufficient rigidity to maintain structural support of the heat cells and to prevent unacceptable stretching of the continuous layer or layers during processing or use.

It is a still further object on the present invention to provide disposable elastic thermal back wraps which provide consistent, convenient and comfortable heat application while ensuring child resistance.

These objectives and additional objectives will become readily apparent from the detailed description which follows.

SUMMARY OF THE INVENTION

The disposable elastic thermal back wrap of the present invention comprises a substantially rectangular piece of flexible material having an outer surface, a body-facing side, a first end, a second end, and an elastic portion between first end and second end, stretchable along a longitudinal axis of the piece of flexible material. The piece of flexible material has a length great enough to encircle a user's waist such that the first and second ends overlap. The first end has a reclosable fastening system for attaching the first end to the piece of flexible material near the second end in order to hold the piece of flexible material around the user's waist.

The elastic thermal back wrap still further comprises one or more thermal packs, preferably embedded in the piece of flexible material, to apply thermal energy to the user's back. The thermal pack or packs comprise a unified structure, comprising at least one continuous layer having a first side comprising polypropylene and a second side comprising a low melt temperature polymer, which has different stiffness characteristics over a range of temperatures and a plurality of individual heat cells spaced apart, which provide a controlled and sustained temperature and which reach their operating temperature range quickly. The heat cells are spaced apart and fixedly attached within each thermal pack. Such thermal pack or packs provide good drapability while maintaining sufficient rigidity, to maintain structural support of the heat cells and to prevent unacceptable stretching of the continuous layer or layers during prosessing or use, providing consistent, convenient and comfortable heat application. Preferably, the heat cells comprise a mixture of powdered iron, powdered carbon, water, and salt, which when exposed to oxygen, provides heat for several hours.

The fastening system has a plurality of hook members which engage loop fibers of a landing zone attached to the piece of flexible material in order to adjust the wrap to a variety of user waist sizes and to attain a comfortable level of elastic tension. The piece of material has a landing zone on the continuous outer surface which is preferably a knitted material, brushed to increase nap and thereby expose a plurality of loop fibers, or a nonwoven material which is puckered to generate a plurality of loop fibers.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 2 is a sectioned side elevation view of FIG. 1.

DETAILED DESCRIPTION OF THE INVENTION

Figure 1:
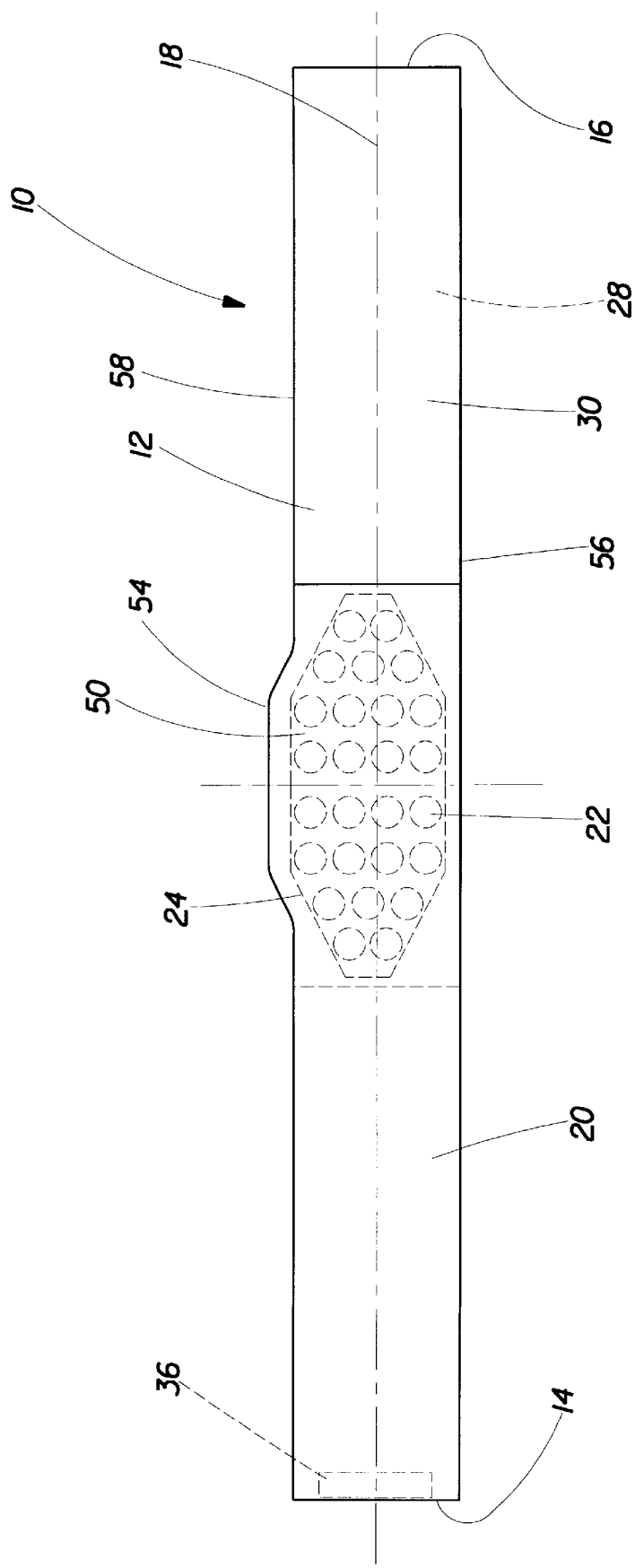
FIG. 1 is a top plan view of a preferred embodiment of the disposable elastic back wrap of the present invention, showing the preferred pattern of thermal pack(s) and/or heat cells embedded therein.

The disposable elastic thermal back wrap of the present invention comprises one or more thermal packs having at least one continuous layer of a material, which exhibits specific thermophysical properties. The material is semirigid when at room temperature, i.e., about 25° C., or below, but softens and becomes substantially less rigid when heated to about 45° C. Therefore, when heat cells, which are fixedly attached to the structure of the thermal pack, are active, that is at a heat cell temperature of from about 39° C. to about 60° C., preferably from about 40° C. to about 48° C., more preferably from about 41° C. to about 47° C., and most preferably from about 42° C. to about 45° C., the narrow portion of the continuous layer or layers of material immediately surrounding each heat cell softens and acts as a hinge between the heat cell and the remaining more rigid portion of the continuous layer or layers, bending preferentially more than either the heat cell or the cooler, more rigid portion. This results in a thermal pack which possesses sufficient rigidity to maintain structural support of the heat cells and prevent unacceptable stretching of structures of the continuous layer or layers during processing or use, while still maintaining good overall drape characteristics when heated. The disposable elastic thermal back wrap of the present invention, provides consistent, convenient, and comfortable heat application, and an excellent conformity to the user's back, while retaining sufficient rigidity to ensure child resistance.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Agglomerated pre-compaction composition", as used herein, means the mixture of dry powdered ingredients, comprising iron powder, carbonaceous powder, metal salt (s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/ solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Semirigid material", as used herein, means a material which is rigid to some degree or in some parts and exhibits a toughness to maintain structural support of the heat cells in an unsupported format, and/or to prevent unacceptable stretching of structures of the material during processing or use and/or to ensure child resistance while still maintaining good overall drape characteristics when heated.

"Two dimensional drape", as used herein, means drape whioch occurs across a continuous layer or layers, across a thermal pack, or across a select region o fa layer or layers, or thermal pack, exclusively along one axis, i.e., one fold line forms, at the expense of other fold lines in response to gravitational pull or other modest forces.

"Three dimensional drape", as used herein, means drape which simultaneously occurs across a continuous layer or layers, across a thermal pack, or across a select region of a layer or layers, or thermal pack, among two or more axes in response to gravitational pull or other modest forces.

It is understood that the disposable elastic thermal back wrap of the present invention may contain one or more thermal packs. For clarity, a single thermal pack will be described.

Referring now to the drawings, and more particularly to FIGS. 1 and 2, there is shown a preferred embodiment of the present invention, which provides a disposable elastic thermal back wrap and is generally indicated as 10. As used herein elastic refers to that property of a material whereby the material, when subjected to a tensile force, will stretch or expand in the direction of the force and will essentially return to its original untensioned dimension upon removal of the force. Elastic back wrap 10 is comprised of a substantially retangular piece of flexible material 12 having a longitudinal axis 18. Flexible material 12 has a first end 14 and a second end 16 and an elastic portion 20 therebetween capable of being stretched along longitudinal axis 18. Flexible material 12 also has a first edge 56 and an opposing second edge 58, both first edge 56 and second edge 58 extending from first end 14 to second end 16. Flexible material 12 further has a length, as measured in a direction parallel to longitudinal axisw 18, which is great enough to encircle a user's waist and allow first end 14 to overlap second end 16 when wrap 10 is stretched around a user. Flexible material 12 of back wrap 10 has a body-facing side 28 and a continuous outer surface 30, both body-facing side 28 and outer surface 30 extending from first end 14 to second end 16.

Preferably, outer surface 30 of wrap 10 contains a landing zone 31. Landing zone 31 comprises a plurality of loop fibers 32 disposed along the extent of landing zone 31 in the direction of longitudinal axis 18. Plurality of loop fibers 32 of landing zone 31 serve as the loop member of a reclosable hook and loop fastening system. As used herein the term reclosable refers to that property of a fastening system which provides for initial closing of the fastening system, a subsequent opening of the fastening system, followed by at least one additional closings of the same fastening system. The subsequent closing of the fastening system may either return the closure to the original position or it may result in a repositioning of the closure from the initial configuration. Body-facing side 28 of flexible material 12 contains a plurality of hooks 34 defining. hook member 36 which is permanently attached to body-facing side 28 adjacent first end 14. As used herein, the term permanently attached is defined as the joining of two or more elements which remain joined during their intended use. Hook member 36 on body-facing side 28, together with plurality of loop fibers 32 on landing zone 31 on outer surface 30, provide a reclosable hook and loop fastening system for securing first end 14 of flexible material 12 to outer surface 30 of flexible material 12 to hold wrap 10 in position when flexible material 12 is stretched around the wearer's waist, with first end 14 overlapping second end 16. This overlapping of flexible material 12 positions hook member 36 on body-facing side 28 over loop fibers 32 of landing zone 31 on outer surface 30. Since loop fibers 32 are disposed continuously along landing zone 31, hook member 36 may be engaged with loop fibers 32 at any position along landing zone 31 of continuous outer surface 30 of flexible material 12.

Preferably, flexible material 12 has a first fibrous layer 60 at outer surface 30, a second fibrous layer 62 at body-facing side 28, and an elastic laminate 63 interposed therebetween. Elastic laminate 63 comprises an elastic member 64, a carrier layer 65 and a bulking layer 66. In a preferred embodiment elastic member 64 is thermally bonded to carrier layer 65 which in turn is attached to bulking layer 66 to form elastic laminate 63. Elastic laminate 63 extends from first end 14 to thermal pack 50.

Bonding of elastic member 64, carrier layer 65, and bulking layer 66 to form elastic laminate 63 may be done in any number of ways including, but not limited to, double sided adhesive tapes, hot melt adhesive, pressure sensitive adhesives, ultrasonic bonding, thermal bonding, pressure bonding, and mixtures thereof. Adhesives, if used, can be applied via hot melt beads, foam, spiral hot melt, melt blown, spray, immersion, transfer, or combinations thereof. Preferably, an adhesive layer 69 is used. Suitable elastic properties can be achieved via a number of construction techniques including, but not limited to, lamination with strained elastic, zero-strain elastics with subsequent activation in either machine direction or cross direction, or a combination of these techniques.

Elastic back wrap 10 further comprises a first stiffening layer 52 and a second stifling layer 53. Stiffening layers 52 and 53 are located adjacent second fibrous layer 62 extending from second end 16 to, and preferably overlapping, elastic laminate 63. Alternatively, a single stiffening layer may be used.

Hooks 34 may be any number of styles, shapes, and/or densities depending upon the use. Hooks 34 may be bent shafts, mushroom capped, harpoon-shaped, or any other suitable shape. Hooks 34 may be unidirectional, bi-directional, or omni-directional depending upon the application and companion loop fibers 32. Hooks 34 must be chosen in conjunction with companion loop fibers 32 so as to provide the peel and shear forces that are required for different applications.

Hook member 36 and loop fibers 32 ideally are chosen to provide shear strength greater than the elastic tension exerted by wrap 10 during use. Hook member 36, found to work particularly well, comprises harpoon shaped hooks 34, which are oriented parallel to longitudinal axis 18 of material 12. Such hooks are available as 960E from Aplix, Charlotte, N.C. Hooks 34 are permanently attached to back wrap 10 by means of ultrasonic bonding, pressure bonding, adhesives, and/or stitching.

Landing zone 31 comprising loop fibers 32 may be any number of materials including, but not limited to, woven, knit, and nonwoven materials that have either been formed with loop fiber or have been subjected to post processing such as brushing or napping to expose more loop fibers. A preferred material is knit nylon landing zone material available as style #18904 from Guilford Fabrics, Greensboro, N.C.

First fibrous layer 60 and second fibrous layer 62 may be any number of different materials including, but not limited to, wovens, knits, carded nonwovens, spunbond nonwovens, and the like. These fabrics may be made of either natural or synthetic fibers including, but not limited to, polypropylene, polyethylene, polyester, nylon, rayon, cotton, cellulose, and the like. A material that has been successfully used is a 27 grams per square yard (gsy) thermally bonded carded polypropylene nonwoven available as grade #9327786 from Veratec, Walpole, Mass.

Carrier layer 65 may be selected from any number of materials that are capable of withstanding thermal bonding temperature and sufficiently strong to carry elastic member 64. These materials include, but are not limited to, wovens, knits, carded nonwovens, spunbond nonwovens, and the like. These fabrics may be made of either natural or synthetic fibers including, but not limited to, polypropylene, polyester, nylon, rayon, cotton, cellulose, and the like. A material that has been successfully used is a 27 gsy thermally bonded carded polypropylene nonwoven available as grade #9327786 from Veratec, Walpole, Mass.

Elastic member 64 can be selected from natural or synthetic rubber, or any number of polymeric materials which are capable of elongation and recovery.

Suitable materials include, but are not limited to, Styrene Block Copolymers, rubber, Lycra™, (a trademark of E. I. DuPont De Nemours, Wilmington, Del.), and Krayton™ (a trademark of Shell Oil Co., Houston, Tex.). They may also include polyethylenes including metallocene catalyst PE, foams including polyurethane and polyester, and the like. Elastic member 64 can be in the form of: strands, scrims, ribbons, tapes, structural elastic-like films. A material that has been used successfully is a polyurethane elastic scrim available as T50018 from Conwed Plastics, Minneapolis, Minn.

Bulking layer 66 may be any number of different materials including, but not limited to, woven or knit fabrics, formed films, carded nonwovens, spunbond nonwovens, and the like. A material that has been found to be particularly suitable for bulking layer 66 is a polyethylene formed film available as C3265 from Tredeger Film Products, Terre Haute, Ind.

First stiffening layer 52 and second stiffening layer 53 may be chosen from any number of suitable materials which provide added rigidity in a direction transverse longitudinal axis 18. Suitable materails include, but are not limited to, wovens, knits, carded nonwovens, spunbond nonwovens, meltblown, combinations thereof, and the like. These fabrics may be made of either natural or snythetic fibers including, but not limited to, polypropylene, polyester, nylon, rayon, cotton, cellulose, combinations thereof, and the like. These materials may be post processed to increase their stiffness. This post processing may include calandering, embossing, bonding, and the like. A material which has been used successfully for first stiffening layer 52 is a spunbond/meltblown/spunbond (SMS) laminate available as Ultramesh Grade #L4990.4, form Veratec, Walpole, Mass. A material which has been used successfully for second stiffening layer 53 is a 35 gsy polypropylene spunbond available as 35 gsy Veraspun, grade #91061, from Veratec, Walpole, Mass.

Attachment of the various layers to make back wrap 10 may be achieved by any number of attachment means known in the art. These include, but are not limited to, hot melt adhesive including spiral sprays, meltblown, control coat, and the like, latex adhesives applied via spray, printing, gravure, and the like, thermal bonding, ultrasonic, pressure bonding, and the like. Preferably, an adhesive layer 69 is used. One particular method that has been used successfully for adhesive layer 69 is a hot melt adhesive available as 70-4589 from National Starch and Chemical Co., Bridgewater, N.J., applied via a spiral hot melt system at a rate of from 5 to 10 mg per square inch.

Elastic back wrap 10 also includes thermal pack 50. Thermal pack 50 comprises a plurality of individual heat cells 22 arranged in a substantially planar diamond-shaped pattern, as indicated by dotted line 24, and a lower flap portion 54 extending outwardly from second edge 58. Heat cells 22 are depicted in FIG. 1 extending into lower flap portion 54 which is intended to position heat cells 22 low on the back of the user. Alternatively, lower flap portion 54 may be omitted and heat cells 22 repositioned on wrap 10 so as to be contained entirely between first edge 56 and second edge 58. The dimensions of pattern 24 are about 225 mm to about 300 mm measured in a direction parallel to transverse axis 18 and about 115 mm to about 200 mm measured in a direction transverse to longitudinal axis 18.

Each thermal pack 50 comprises a plurality of individual heat cells 22, preferably embedded within the laminate structure of the thermal pack 50. These heat cells 22 are spaced apart from each other and each heat cell 22 functions independently of the rest of the heat cells 22. Each heat cell 22 contains a densely packed, particulate exothermic composition 74 which substantially fills the available cell volume within the cell reducing any excess void volume thereby minimizing the ability of the particulate matter to shift within the cell. Alternatively, the exothermic composition 74 may be compressed into a hard tablet before being placed in each cell. Because the heat generating material is densely packed or compressed into a tablet, the heat cells 22 are not readily flexible. Therefore, the spacing apart of the cells and the materials selected for cell forming base layer 70 and cell covering layer 72 between the heat cells 22 allows each thermal pack 50 to easily conform to the user's body.

Alternatively, each thermal pack 50 may comprise a single continuous base layer 70, wherein individual heat cells 22 are fixedly attached and spaced apart across the base layer 70.

Cell forming base layer 70 and cell covering layer 72 may be made of any number of thermoplastic materials which are semirigid at a temperature of about 25° C. and which soften, i.e., become substantially less rigid, at a temperature of about 45° C. Different materials may be capable of satisfing the specified requirement provided that the thickness is adjusted accordingly. Such materials include, but are not limited to, films of polyethylene, polypropylene, polyester, styrene block copolymers, film coated nonwovens, laminates, permeable membranes, and mixtures thereof. These materials may be used alone or coextruded with a low melt temperature polymer including, but not limited to, ethylene vinyl acetate copolymer, low density polyethylene, and mixtures thereof. Such materials are also capable of containing exothermic composition 74 may limit oxygen flow into heat cell 22 and provide sufficient rigidity to prevent wrap 10 from folding or bunching during use, to prevent unacceptable stretching of structures of the continuous layer during processing or use, and to ensure child resistance.

Cell forming base layer 70 and cell covering layer 72 are preferably comprised of a coextruded film, having a first side of polypropylene and a second side of EVA, and having a combined thickness of from about 20 $\mu$m to about 30 $\mu$m, preferably about 25 $\mu$m. The polypropylene comprises form about 10% to about 90%, preferably from about 40% to about 60%, of the thickness of cell forming base layer 70 and cell covering layer 72. When coextruded films of the type just described are used for cell forming base layer 70 and cell covering layer 72, the EVA sides are preferably orientied toward each other to facilitate thermal bonding of cell covering layer 72 to cell forming base layer 70. A particularly suitable material is available as P18-3161 from Clopay Plastics Products, Cincinnati, Ohio, or Terre Haute, Ind. The P18-3161 which is suitable for cell covering layer 72 has been subjected to a post process aperturing with hot needles to render it permeable to oxygen.

When coextruded films of the type just described are used for cell forming base layer 70 and cell covering layer 72, the EVA sides are preferably oriented toward each other to facilitate thermal bonding of cell covering layer 72 to cell forming base layer 70.

Exothermic composition 74 may comprise any composition capable of providing heat. However, exothermic composition 74 preferably comprises a particulate mix of chemical compounds that undergo an oxidation reaction during use. Exothermic composition 74 may also be formed into agglomerated granules, direct compacted into compaction articles such as granules, pellets, tablets, and/or slugs, and mixtures thereof The mix of compounds typically comprises iron powder, carbon, a metal salt(s), and water. Mixtures of this type react when exposed to oxygen provide heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, nonactivated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used.

Typically, the additional water-holding materials comprise from about 0.1% to about 30% by weight, preferably from about 5% to about 20% by weight, most preferably from about 1% to about 10% by weight, of the particulate exothermic composition.

Other additional components include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and $\alpha$-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

The heat cells 22 of each thermal pack 50 can have any geometric shape, e.g., disk, triangle, pyramid, cone, sphere, square, cube, rectangle, rectangular parallelepiped, cylinder, ellipsoid and the like. The preferred shape of the heat cells comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm.

The heat cells 75 have a height of from about 0.08 cm to about 1 cm, preferably from about 0.15 cm to about 0.9 cm, more preferably greather than from about 0.2 cm to about 0.8 cm, and most preferably about 0.4 cm.

The ratio of fill volume to cell volume of the heat cells 22 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability in cell covering layer 72 is preferably a plurality of apertures in cell covering layer 72, which are made by piercing cell covering layer 72 with hot needles. The size of the apertures is preferably about 0.127 mm diameter, and there are preferably 25 to 40 apertures per heat cell 22. Another preferred method of making apertures is to pierce cell covering layer 72 with cold needles. Alternatively, apertures may be produced by a vacuum forming or a high pressure water jet forming process. Yet another method is making cell covering layer 72 from a microporous membrane or a semipermeable membrane. Such membrane may be combined with a highly porous carrier material to facilitate processing. The oxygen permeability required ranges from about 0.01 cc $O_2$ per minute per 5 square cm to about 15 cc $O_2$ per minute per 5 square cm at 21° C. and 1 atm.

Using the materials described above for construction of wrap 10, most people can be accommodated with only two different sizes of wrap 10. The smaller size of wrap 10 has a dimension of about 915 mm measured in a direction parallel to the longitudinal axis 18 when wrap 10 is in a relaxed or untensioned state and a dimension of about 125 mm to about 150 mm measured in a direction transverse to the longitudinal axis 18. The larger size of wrap 10 has a dimension of about 1100 mm measured in a direction parallel to the longitudinal axis 18 when wrap 10 is in a relaxed or untensioned state and a dimension of about 135 mm to about 150 mm measured in a direction transverse to the longitudinal axis 18. These two sizes of wrap 10 will accommodate most people with waist sizes of less than about 1220 mm.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable elastic thermal back wrap comprising:
   a) at least one substantially rectangular piece of flexible material having a first end, a second end, a longitudinal axis running between said first end and said second end, a first edge and an opposing second edge running between said first end and said second end axial said longitudinal axis, one or more elastic portions between said first end and said second end wherein said elastic portion is stretchable along said longitudinal axis, and a length great enough to encircle a user's waist such that said first and second ends overlap;
   b) one or more thermal packs fixed within or to said piece of flexible material, which comprise a unified structure of at least one continuous layer, which consists essentially of a coextruded material having a first side of polypropylene and a second side of a low melt temperature copolymer wherein said continuous layer is semirigid at a temperature of about 25° C. and substantially less rigid at a temperature of about 45° C., and a plurality of individual heat cells spaced apart and fixed within or to said unified structure of said thermal pack; and
   c) a fastening system in order to hold said at least one piece of flexible material around said user's waist.

2. A disposable elastic thermal back wrap according to claim 1 wherein said continuous layer comprises a coextruded film having a first side of polypropylene and a second side of ethylene vinyl acetate copolymer, wherein said polypropylene comprises from about 10% to about 90% of the total thickness of said film.

3. A disposable elastic thermal back wrap according to claim 2 wherein said continuous layer comprises a coextruded film having a first side of polypropylene and a second side of ethylene vinyl acetate copolymer, wherein said polypropylene comprises from about 40% to about 60% of the total thickness of said film.

4. A disposable elastic thermal back wrap according to claim 3 wherein said continuous layer has a thickness of from about 20 $\mu$m to about 30 $\mu$m.

5. A disposable elastic thermal back wrap according to claim 1 wherein said fastening system is reclosable.

6. A disposable elastic thermal back wrap according to claim 5 wherein said reclosable fastening system comprises a hook and loop fastening system.

7. A disposable elastic thermal back wrap according to claim 1 wherein said individual heat cells are arranged in a substantially planar diamond shaped pattern.

8. A disposable elastic thermal back wrap according to claim 1 further comprising a lower flap portion extending outwardly from said second edge.

9. A disposable elastic thermal back wrap according to claim 1 wherein said disposable elastic thermal back wrap further comprises one or more stiffening layers.

10. A disposable elastic thermal back wrap according to claim 1 wherein said heat cells comprise an exothermic composition which comprises:
    a.) from about 30% to about 80% iron powder;
    b.) from about 3% to about 25% activated carbon, non-activated carbon, and mixtures thereof;
    c.) from about 0.5% to about 10% metal salt; and
    d.) from about 1% to about 40% water.

11. A disposable elastic thermal back wrap according to claim 10 wherein said heat cells comprise from about 0.1% to about 30% of additional water-holding material.

12. A disposable elastic thermal back wrap according to claim 10 wherein said heat cells comprise a shape selected from the group consisting of a disk, triangle, pyramid, cone, sphere, square, cube, rectangle, rectangular parallelepiped, cylinder, and ellipsoid.

13. A disposable elastic thermal back wrap according to claim 12 wherein said heat cells comprise the shape of a disk having a diameter of from about 0.2 cm to about 10 cm and a height of greater than from about 0.2 cm to about 1.0 cm.

14. A disposable elastic thermal back wrap according to claim 1 wherein said heat cells comprise an exothermic composition which comprises:
    a.) from about 30% to about 80% of iron powder;
    b.) from about 3% to about 20% of carbonaceous material selected from the group consisting of activated carbon, non-activated carbon, and mixtures thereof;
    c.) from about 0% to about 9% of an agglomeration aid selected from the group consisting of corn syrup, maltitol syrup, crystallizing sorbitol syrup, amorphous sorbitol syrup, and mixtures thereof; and
    d.) from about 0% to about 35 % of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;

wherein from about 0.5% to about 10% of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof.

15. A disposable elastic thermal back wrap according to claim 14 wherein said heat cells further comprise from about 0.5% to about 10% of additional water-holding materials selected from the group consisting of acrylic acid salt starch co-polymer, isobutylene maleic anhydride co-polymer, vermiculite, carboxymethylcellulose, and mixtures thereof.

16. A disposable elastic thermal back wrap according to claim 14 wherein said dry binder comprises from about 4% to about 30% of microcrystalline cellulose.

17. A disposable elastic thermal back wrap according to claim 14 wherein said metal salt comprises sodium chloride.

18. A disposable elastic thermal back wrap according to claim 14 wherein said exothermic composition further comprises from about 1% to about 40% by weight, of water.

19. A disposable elastic thermal back wrap according to claim 14 wherein said direct compaction articles are selected from the group consisting of granules, pellets, tablets, slugs, and mixtures thereof wherein said tablets and slugs comprise a geometric shape selected from the group consisting of disk, triangle, square, cube, rectangle, cylinder, and ellipsoid.

20. A disposable elastic thermal back wrap according to claim 19 wherein said tablets and slugs comprise a disk shaped geometry having a diameter of from about 0.2 cm to about 10 cm and a height of from about 0.08 cm to about 1.0 cm.

21. A disposable elastic thermal back wrap according to claim 19 wherein said direct compaction articles comprise a density of greater than about 1 $g/cm^3$.

22. A disposable elastic thermal back wrap according to claim 21 wherein said direct compaction articles comprise a density of from about 1.5 $g/cm^3$ to about 3.0 $g/cm^3$.

23. A method of treating temporary or chronic lower back pain by applying a disposable thermal back wrap of claim 1 to the lower back of a person needing such treatment.

* * * * *